US012521485B2

(12) United States Patent
Slaby et al.

(10) Patent No.: US 12,521,485 B2
(45) Date of Patent: Jan. 13, 2026

(54) OCCLUSION FORCE REDUCTION THROUGH MULTI- DIRECTIONAL TOLERANCE CONTROL

(71) Applicants: BAXTER INTERNATIONAL INC., Deerfield, IL (US); BAXTER HEALTHCARE SA, Glattpark (CH)

(72) Inventors: Jiri Slaby, Buffalo Grove, IL (US); Steve Pippin, Libertyville, IL (US); Kendall Dean Yeager, Palatine, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 1146 days.

(21) Appl. No.: 17/325,843

(22) Filed: May 20, 2021

(65) Prior Publication Data

US 2021/0361860 A1 Nov. 25, 2021

Related U.S. Application Data

(60) Provisional application No. 63/028,055, filed on May 21, 2020.

(51) Int. Cl.

*A61M 5/168* (2006.01)

*A61M 5/142* (2006.01)

(Continued)

(52) U.S. Cl.

CPC ........ *A61M 5/16813* (2013.01); *A61M 5/142* (2013.01); *A61M 2205/8206* (2013.01)

(58) Field of Classification Search

CPC .............. A61M 5/16813; A61M 5/142; A61M 2205/8206; A61M 5/14; A61M 5/14212;

(Continued)

(56) References Cited

U.S. PATENT DOCUMENTS 5,888,052 A 3/1999 Hill
6,139,531 A 10/2000 Danby
(Continued)

FOREIGN PATENT DOCUMENTS

JP 2001520723 A 10/2001
WO 9734084 A1 9/1997
(Continued)

OTHER PUBLICATIONS

European Rule 161(1) and 162 Communication for corresponding European Patent Application No. 21739469.1, dated Jan. 4, 2023.

(Continued)

*Primary Examiner* — Jason E Flick
(74) *Attorney, Agent, or Firm* — K&L Gates LLP

(57) ABSTRACT

An infusion pumping mechanism includes a motor, a plurality of pump fingers and an opposing plate. Each finger of the pump fingers includes a body portion and a head portion. The head portion includes a tip that is configured to contact and occlude a tube installed in the pumping mechanism. The opposing plate includes an anvil with a plurality of force concentrators. A force concentrator of the plurality of force concentrators corresponds to a respective pump finger of the plurality of pump fingers. Additionally, the force concentrator includes a concentration surface configured to contact and occlude the tube. The force concentrator is aligned with a tip of the respective pump finger such that as the finger is directed towards the tube and contacts the tube, both the tip and the force concentrator provide pressure to opposite sides of the tube and at least partially occlude the tube.

20 Claims, 18 Drawing Sheets

(51) Int. Cl.
*F04B 43/08* (2006.01)
*F04B 43/12* (2006.01)

(58) Field of Classification Search
CPC .......... A61M 5/16804; A61M 2205/82; A61M 5/14228; A61M 60/284; A61M 2005/14506; A61M 60/438; F04B 43/00; F04B 43/08; F04B 43/082; F04B 43/12
See application file for complete search history.

(56) References Cited

U.S. PATENT DOCUMENTS

| | | | | |
|---|---|---|---|---|
| 8,777,597 | B1 | 7/2014 | Geschwender | |
| 11,904,133 | B2 * | 2/2024 | Adams | F04B 43/12 |
| 2014/0243745 | A1 * | 8/2014 | Ueda | A61M 5/16813 604/151 |
| 2020/0139044 | A1 | 5/2020 | Kono et al. | |

FOREIGN PATENT DOCUMENTS

| | | | |
|---|---|---|---|
| WO | 2008059492 | A1 | 5/2008 |
| WO | 2008059492 | A2 | 5/2008 |

OTHER PUBLICATIONS

Colombian Office Action from corresponding Colombian Patent Application No. NC2022/0015866, mailed Jul. 24, 2024. 10 pages.
International Preliminary Report on Patentability for International Application PCT/US2021/033341 dated Nov. 17, 2022.
Canadian Examination Report for corresponding Canadian Patent Application No. 3,177,036, dated Jan. 31, 2024. 4 pages.
English Translation of Notice of Reasons for Rejection from corresponding Japanese Patent Application No. 2022-569105, mailed Feb. 4, 2025. 7 pages.
Office Action for related Mexican Application No. MX/a/2022/014579; action dated Sep. 12, 2025; (7 pages).

* cited by examiner

OCCLUSION FORCE REDUCTION THROUGH MULTI- DIRECTIONAL TOLERANCE CONTROL

RELATED APPLICATIONS

This application claims the benefit of and priority to U.S. Provisional Patent Application No. 63/028,055 filed May 21, 2020, entitled "OCCLUSION FORCE REDUCTION THROUGH MULTI-DIRECTIONAL TOLERANCE CONTROL", which is incorporated herein by reference in its entirety.

BACKGROUND

The present invention relates to a pump and more particularly to an infusion pump for the delivery of a medication to a patient. Generally, medical patients sometimes require precise delivery of either continuous medication or medication at set periodic intervals. Medical pumps have been developed to provide controlled drug infusion wherein the drug can be administered at a precise rate that keeps the drug concentration within a therapeutic margin and out of an unnecessary or possibly toxic range. Basically, the medical pumps provide appropriate drug delivery to the patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in solution over relatively short periods such as from 30 minutes to two hours. These conditions and others have combined to promote the development of increasingly lightweight, portable or ambulatory infusion pumps that can be worn by a patient and are capable of administering a continuous supply of medication at a desired rate, or providing several doses of medication at scheduled intervals.

Configurations of infusion pumps include elastomeric pumps, which squeeze solution from flexible containers, such as balloons, into IV tubing for delivery to the patient. Alternatively, spring-loaded pumps pressurize the solution containers or reservoirs. Certain pump designs utilize cartridges containing flexible compartments that are squeezed by pressure rollers for discharging the solutions. Infusion pumps utilizing syringes are also known wherein a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Additionally, some infusion pumps are portable, for example, an infusion pump may be smaller and more compact for mobile use by ambulatory patients or other patients. Naturally, a portable pump must be supplied with an equally portable power source as a means for powering the pump motor. Batteries are a suitable choice of power for portable units. Some pumps may use disposable batteries while other pumps may use rechargeable batteries. As the operation of such pumps can be critical for life support, they are generally provided with battery back-up. The efficiency of the device thus becomes an important factor because the pump's operational battery life (e.g., length of time the pump can remain in operation while on battery power) is limited by its efficiency.

Multiple needs exist to minimize size and power consumption from an ambulatory infusion pump while maximizing the operational life (e.g., battery life) of the pumping mechanism. Specifically, a need exists to provide a pump that is capable of occluding a pumping conduit such as an IV tube set with a lesser amount of force than existing pumps to extend the operational life (e.g., battery life) of the infusion pump, create lighter components, lighter pumps, especially for ambulatory infusion pumps.

SUMMARY

The instant invention provides for an infusion pump with occlusion force reduction through multi-directional tolerance control. The pump includes guiding features and force concentrators to reduce the necessary occlusion force of the pumping mechanism, which advantageously extends the operational life (e.g., battery life) of the infusion pump.

Aspects of the subject matter described herein may be useful alone or in combination with one or more other aspects described herein. In a first aspect, which may be used with any other aspect described herein, an infusion pumping mechanism includes a motor, a plurality of pump fingers and an opposing plate. Each finger of the plurality of the pump fingers includes a body portion and a head portion. The head portion includes a tip that is configured to contact and occlude a tube installed in the pumping mechanism. The opposing plate includes an anvil with a plurality of force concentrators. A force concentrator of the plurality of force concentrators corresponds to a respective pump finger of the plurality of pump fingers. Additionally, the force concentrator includes a concentration surface configured to contact and occlude the tube. The force concentrator is aligned with a tip of the respective pump finger such that as the finger is directed towards the tube and contacts the tube, both the tip and the force concentrator provide pressure to opposite sides of the tube and at least partially occlude the tube.

In a second aspect, which may be used with any other aspect described herein, the mechanism is part of an infusion pump.

In a third aspect, which may be used with any other aspect described herein, the infusion pump is an ambulatory infusion pump.

In a fourth aspect, which may be used with any other aspect described herein, each finger includes a guide rail and the opposing plate includes corresponding guide slots.

In a fifth aspect, which may be used with any other aspect described herein, each finger includes at least one of guide slot and a guide channel and the opposing plate includes corresponding guide rails.

In a sixth aspect, which may be used with any other aspect described herein, the opposing plate includes guide channels corresponding to each pump finger of the plurality of pump fingers.

In a seventh aspect, which may be used with any other aspect described herein, the guide channel is sized and shaped to receive a portion of a respective pump finger. Additionally, the guide channel is configured to align the pump finger to direct the tip of the respective pump finger towards a corresponding force concentrator.

In an eight aspect, which may be used with any other aspect described herein, each finger includes a guide rail, the opposing plate includes corresponding guide slots, and the opposing plate includes guide channels.

In a ninth aspect, which may be used with any other aspect described herein, the guide channel is sized and shaped to receive a portion of a respective pump finger. Additionally, the guide slot is sized and shaped to receive at least a portion of a respective guide rail to direct the tip of the respective pump finger towards a corresponding force concentrator.

In a tenth aspect, which may be used with any other aspect described herein, each respective force concentrator is made of an elastic material.

In an eleventh aspect, which may be used with any other aspect described herein, each respective force concentrator is non-compressible.

In a twelfth aspect, which may be used with any other aspect described herein, an infusion pump includes a power source, a pumping mechanism, and an infusion tube set with a pumping conduit. The pumping mechanism includes at least one pump finger and an opposing plate with at least one force concentrator. The at least one pump finger includes a body portion and a head portion. Additionally, the head portion includes a tip that is configured to contact and occlude the pumping conduit. The at least one force concentrator is axially aligned with the at least one pump finger, and the at least one force concentrator includes a concentration surface configured to contact and occlude the pumping conduit opposite of the tip of the at least one pump finger.

In a thirteenth aspect, which may be used with any other aspect described herein, the infusion pump is an ambulatory infusion pump.

In a fourteenth aspect, which may be used with any other aspect described herein, the at least one pump finger includes at least one of a guide channel and a guide slot.

In a fifteenth aspect, which may be used with any other aspect described herein, the opposing plate includes a guide rail corresponding to at least one of the guide channel and the guide slot.

In a sixteenth aspect, which may be used with any other aspect described herein, the at least one pump finger includes a guide rail.

In a seventeenth aspect, which may be used with any other aspect described herein, the opposing plate includes a guide slot corresponding to the guide rail.

In an eighteenth aspect, which may be used with any other aspect described herein, the opposing plate includes at least one guide channel corresponding to the at least one pump finger.

In a nineteenth aspect, which may be used with any other aspect described herein, the at least one guide channel is sized and shaped to receive a portion of the at least one pump finger. Additionally, the guide slot is sized and shaped to receive the guide rail to direct the tip of the respective pump finger towards a corresponding force concentrator.

In a twentieth aspect, which may be used with any other aspect described herein, the at least one force concentrator is made of an elastic material.

In a twenty-first aspect, which may be used with any other aspect described herein, the at least one force concentrator is non-compressible.

In a twenty-second aspect, which may be used with any other aspect described herein, the pumping conduit comprises a tube.

In a twenty-third aspect, which may be used with any other aspect described herein, the pumping conduit includes a silicon membrane.

Therefore, it is a primary object of the invention to provide for an infusion pump with improved operational life (e.g., battery life).

It is another object of the invention to provide an infusion pump with lighter components resulting in a lighter infusion pump.

It is yet another object of the present invention to provide alignment and guiding features to assist with tube occlusion.

It is another object of the invention to reduce the force required for tube occlusion in an infusion pump.

Additional features and advantages of the disclosed infusion pump are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

The below disclosure relates to an infusion delivery system, such as an infusion pump, which is used to deliver fluids (e.g., medications or nutrients) to a patient in predetermined quantities. The infusion pump may be an ambulatory pump. To minimize ambulatory pump size and power consumption while maximizing the operational life of the pumping mechanism, the systems and techniques disclosed herein allow for a pumping conduit such as an IV tube set to be occluded with minimal force. Occluding the tube set with minimal force is especially important for ambulatory pumps because of the pump's longer term portability. The longer term portability typically is associated with smaller pump sizes for ambulatory infusion pumps and therefore the motors and pumping mechanisms are restricted to smaller spatial restrains (e.g., small envelopes of space) than other types of infusion pumps.

Figure 1A:
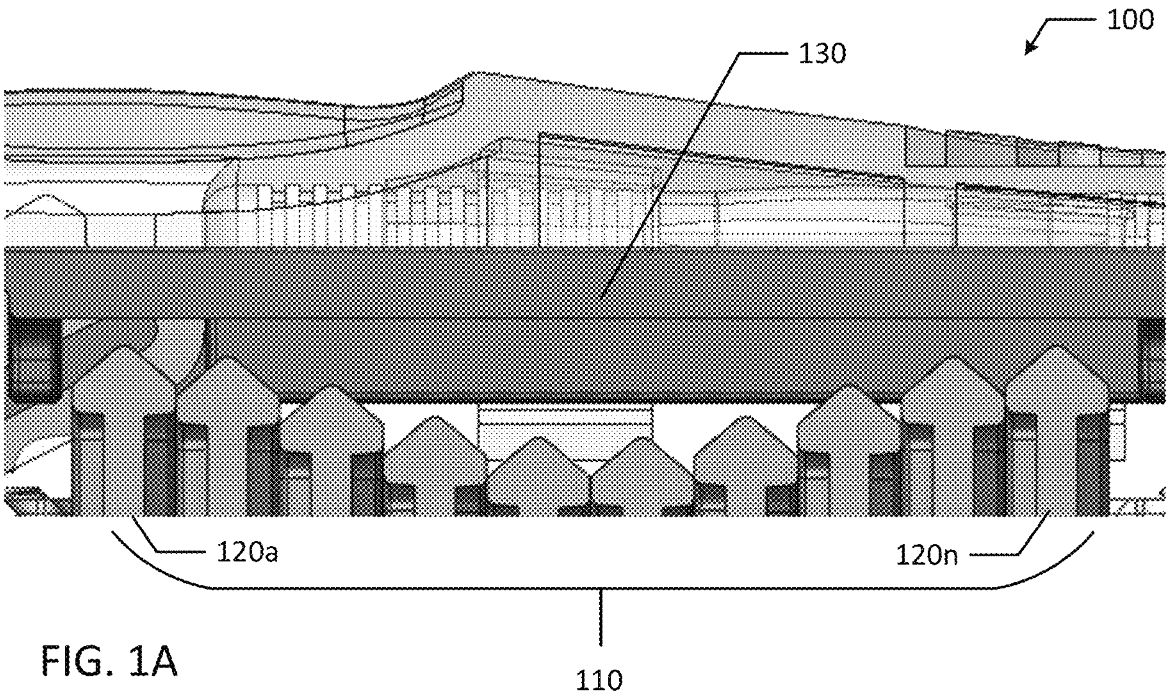
FIG. 1A is a partial side view of a pumping mechanism according to an example embodiment of the present disclosure.

FIG. 1A illustrates a pumping mechanism 100 without an IV tube set loaded. In the illustrated example, the pumping mechanism 100 includes ten (10) mechanism fingers 120*a-n* that form a pumping section 110 of the pumping mechanism 100. The pumping mechanism 100 also includes an opposing plate 130 (e.g., a cassette back plate, anvil, door).

Figure 1B:
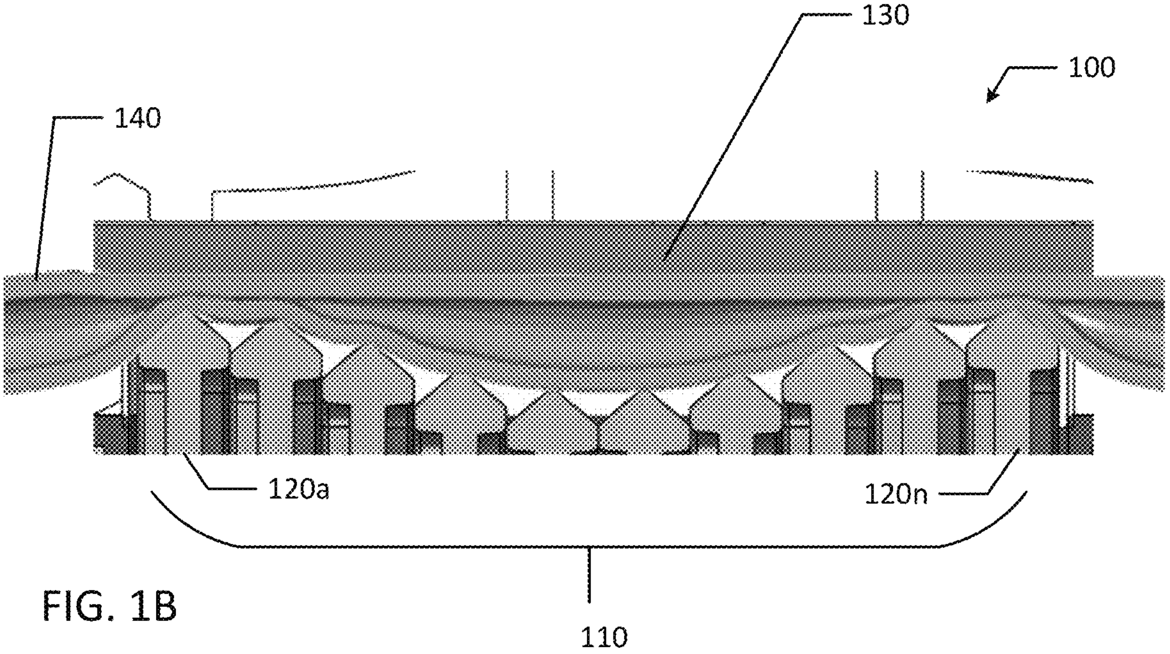
FIG. 1B is a partial side view of the pumping mechanism of FIG. 1A with a pumping conduit according to an example embodiment of the present disclosure.

FIG. 1B illustrates the pumping mechanism 100 of FIG. 1A with an IV tube set 140 loaded, which is deformed by several of the mechanism fingers 120*a-n*. In the illustrated example, mechanism fingers 120*a* and 120*n* occlude the pumping conduit such as tube 140 at two different locations within the pumping section 110. It should be appreciated that other pumping conduits may be used other than a tube 140. For example, the pumping conduit may provide a flow channel with a flexible membrane. In an example, the flexible membrane or another portion of the pumping conduit may be made of silicone, PVC, or other elastomers.

Figure 1C:
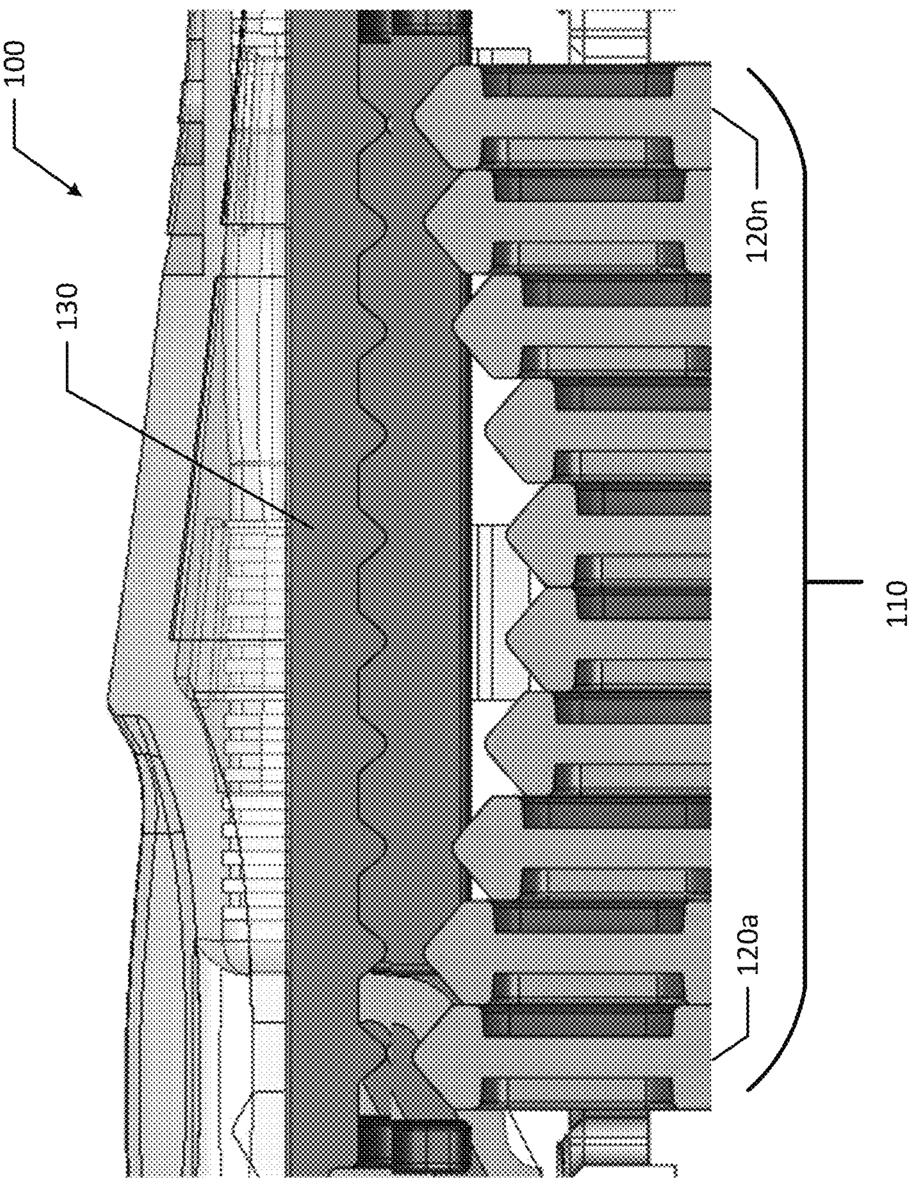
FIG. 1C is a partial side view of another pumping mechanism according to an example embodiment of the present disclosure.

FIG. 1C illustrates a pumping mechanism 100 without an IV tube set loaded. In the illustrated example, the pumping mechanism 100 includes ten (10) mechanism fingers 120*a-n* that form a pumping section 110 of the pumping mechanism 100. The pumping mechanism 100 also includes an opposing plate 130 (e.g., a cassette back plate, anvil, door). In the example illustrated in FIG. 1C, the opposing plate 130 includes force concentrators, which are described in more detail below.

Figure 2A:
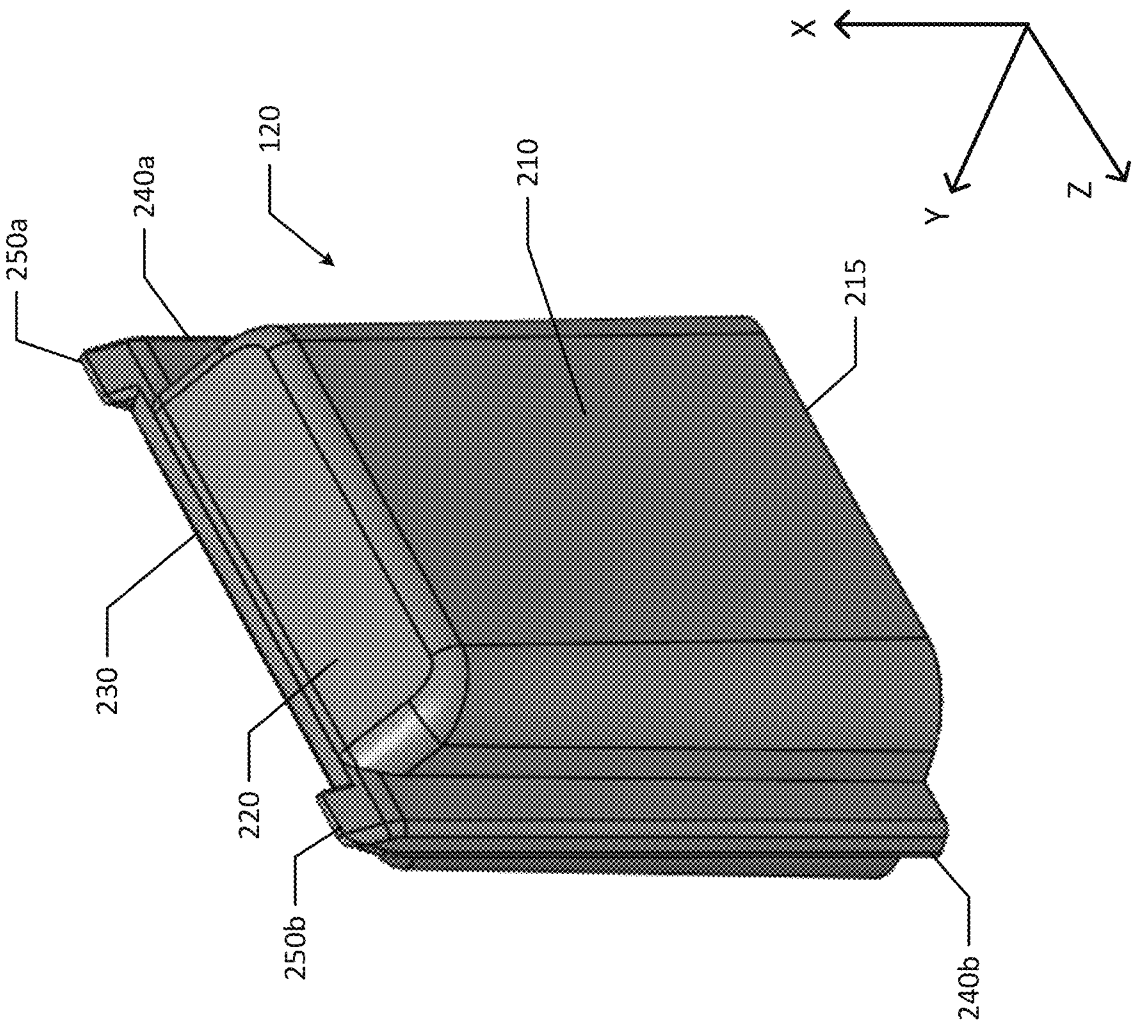
FIGS. 2A, 2B and 2C are perspective views of example pump fingers according to example embodiments of the present disclosure.
Figure 2B:
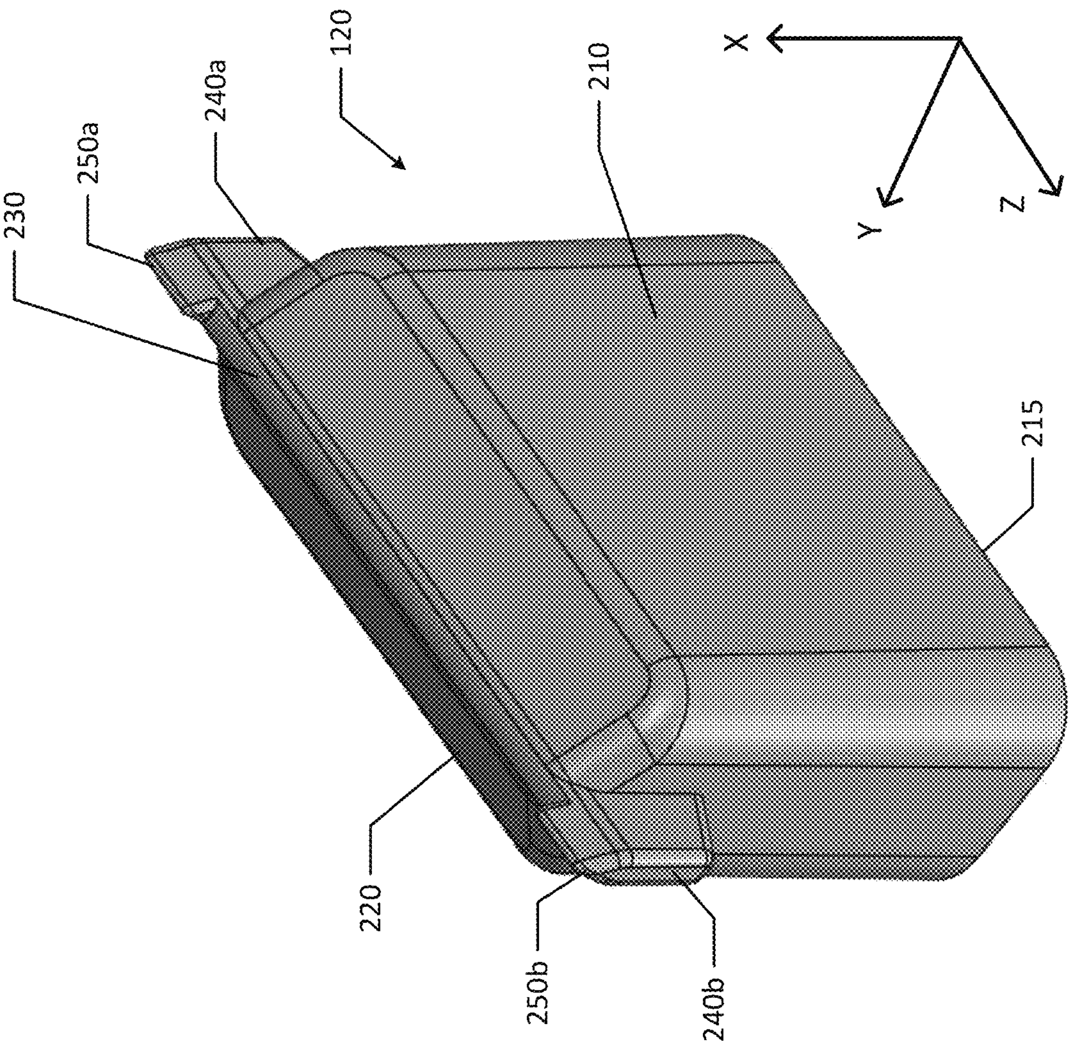

As illustrated in FIGS. 2A and 2B, each finger 120 may include a body portion 210 and a head portion 220. The head portion 220 may include a tip 230 that serves as a force concentrator. For example, the body portion 210 of the finger 120 may have a constant cross-sectional area from a first end 215 of the finger 120 to the start of the head portion 220. Within the head portion 220, the cross sectional area may decrease as the head portion narrows until reaching the tip 230. The narrowing of the head portion 220 creates a tip 230 or force concentration feature on the finger 120. In the illustrated example, the finger 120 also includes guide rails 240*a-b* that are adapted to fit within and move within corresponding guide slots on the cassette (SEE FIGS. 3A, 3B, 3C, 3D, 5A and 5B).

An alternative embodiment may also include a rail in the opposing plate 130 (or other component other than the fingers 120) and a slot in the finger 120. For example, the opposing plate 130 may include guide rails similar to guide rails 240*a-b* and the fingers may include guide slots and/or guide channels similar to guide slots 320 and guide channels 360.

In FIG. 2A, the guide rails 240*a-b* extend along the entire length of the finger 120. Each guide rails 240 includes an additional guide protrusions or stops 250*a-b*. The additional guide protrusions or stops 250*a-b* may be adapted to pre-align each finger 120 prior to substantial compression of the IV tube. Additionally, the guide protrusions or stops 250*a-b* may provide an extended alignment path for the guide rails 240 in areas of limited space. In another example, the guide protrusions or stops 250*a-b* may be adapted to limit the motion of the finger 120 in the X-direction (see FIGS. 5A, 5B and 6A). Limiting the motion of the finger 120 in the X-direction may extend the life of the IV tube set (or other pumping conduit) and ensures that the fingers 120 do not over occlude the tube or press further into the tube 140 than is necessary to achieve an occluded state. In FIG. 2B, the guide rails 240*a-b* extend along a portion of the length of finger 120. By reducing the overall length of the guide rails 240*a-b*, the mass and weight of each finger 120 may be reduced, which may advantageously reduce the amount of power and force to move each finger 120. In FIG. 2B, the guide rails 240*a-b* extend along the sides of the finger 120 in the head portion 220.

Figure 2C:
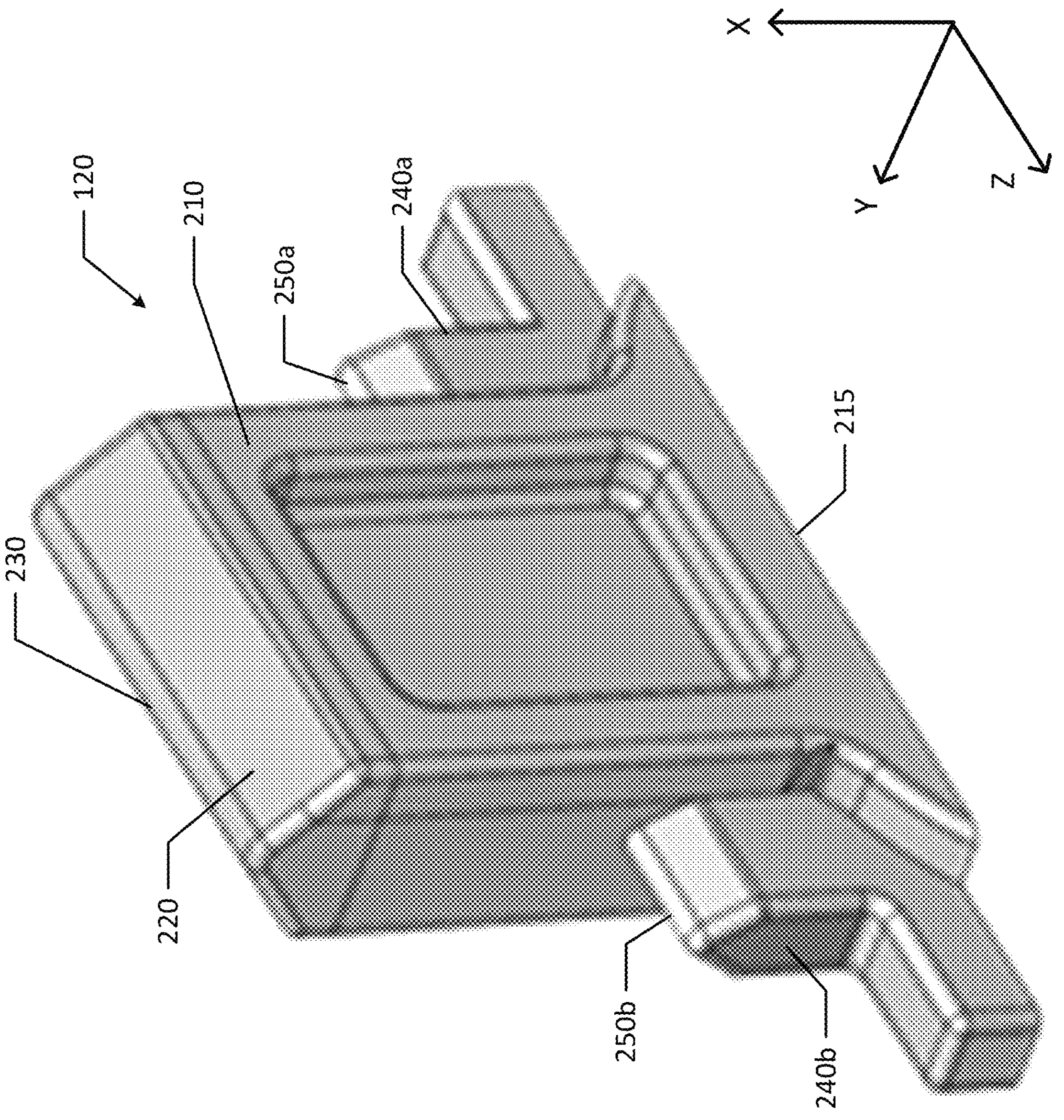

In FIG. 2C, the guide rails 240*a-b* extend along a portion of the length of finger 120, closer to first end 215 of the finger 120 (e.g., lower along the X-direction). The position of the guiding rails 240*a-b* illustrated in FIG. 2C may provide alignment with components other than the opposing plate 130, which advantageously provides alignment and/or sealing in alternate configurations with different components between the fingers 120 and opposing plate 130. For example, the additional guide protrusions or stops 250*a-b* may be adapted to create a seal between each finger 120 and a component between the fingers 120 and opposing plate 130. Additionally, the guide protrusions or stops 250*a-b* may provide an extended alignment path for the guide rails 240.

The guide rails and slots control planar movement in the Y-Z plane to align force concentrators (see force concentrators 330 of FIGS. 3A-3F) with the tips 230 of each finger 120. Additionally, as described in more detail below, the opposing plate 130 may also include force concentrators (see force concentrators 330 of FIGS. 3A-3F) which may be compressible or non-compressible. In an example, compressible or elastomeric force concentrators may be positioned along the opposing plate 130, which advantageously provides control for tolerance compensation in the X-direction As illustrated in FIGS. 3A-3F, guide slots 320 on the cassette 310 provide guidance to the rails 240*a-b* to align the respective head portions 220 and more specifically the respective tips 230 towards respective force concentrators 330 on the back place 130 of the cassette 310. Guiding the tips 230 of fingers 120 to the corresponding concentration surfaces (e.g., tip portions) of the force concentrators 330 also reduces the force required to occlude the IV tube 140 (or other pumping conduit). In an example, guide slots may be used alone without guide rails 240*a-b*. For example, the guide slots 320 may be sized and shaped to accommodate either the head portion 220 or the body portion 210 to guide the motion of fingers 120, as further illustrated by guide channels 360 in FIGS. 3D and 3E. In other examples, both finger guide rails 240 and associated finger guide slots 320 may be used to pre-align the tip 230 of each finger with corresponding force concentrators 330. Additionally, guide channels 360 may be used along with guide slots 320 to provide additional alignment for fingers 120. In some cases, the guide slots and/or the guide channels may work in unison to ensure proper final alignment of the tip 230 as finger 120 advances toward the force concentrator 330 to minimize the required occlusion force.

Figure 3B:
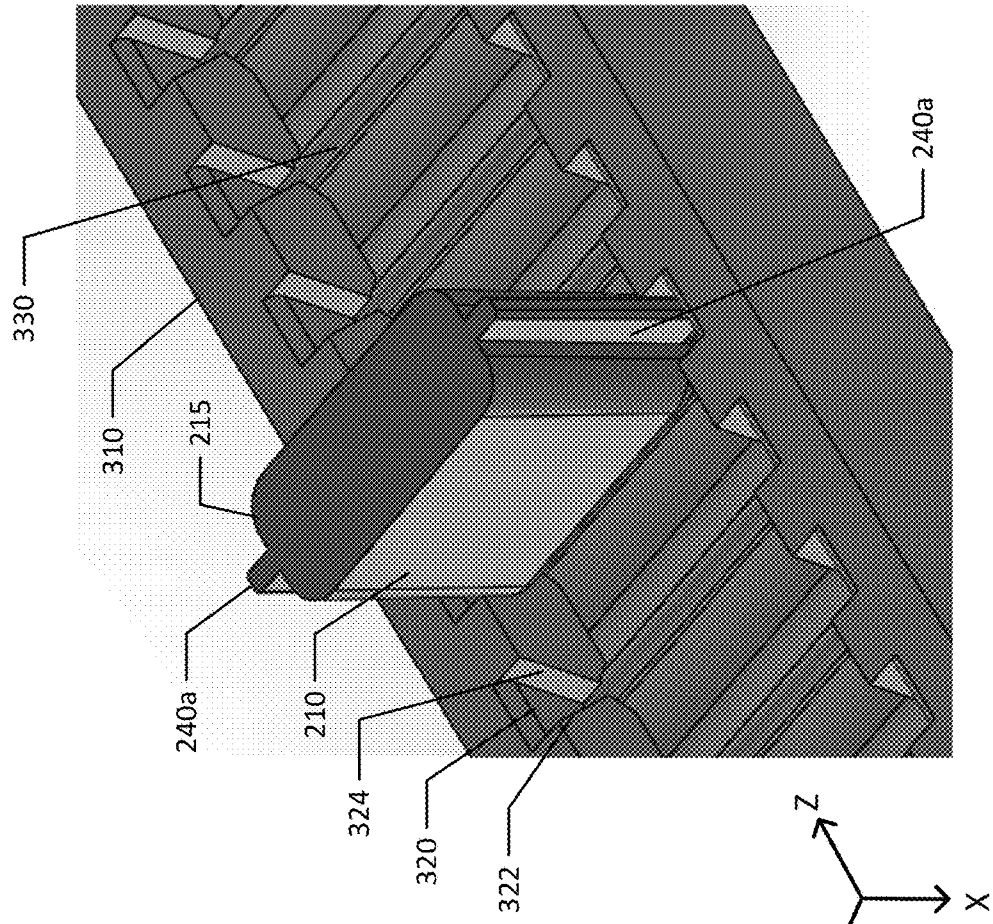
FIG. 3B is a partial perspective view of an opposing plate and pump finger according to example embodiments of the present disclosure.
Figure 3A:
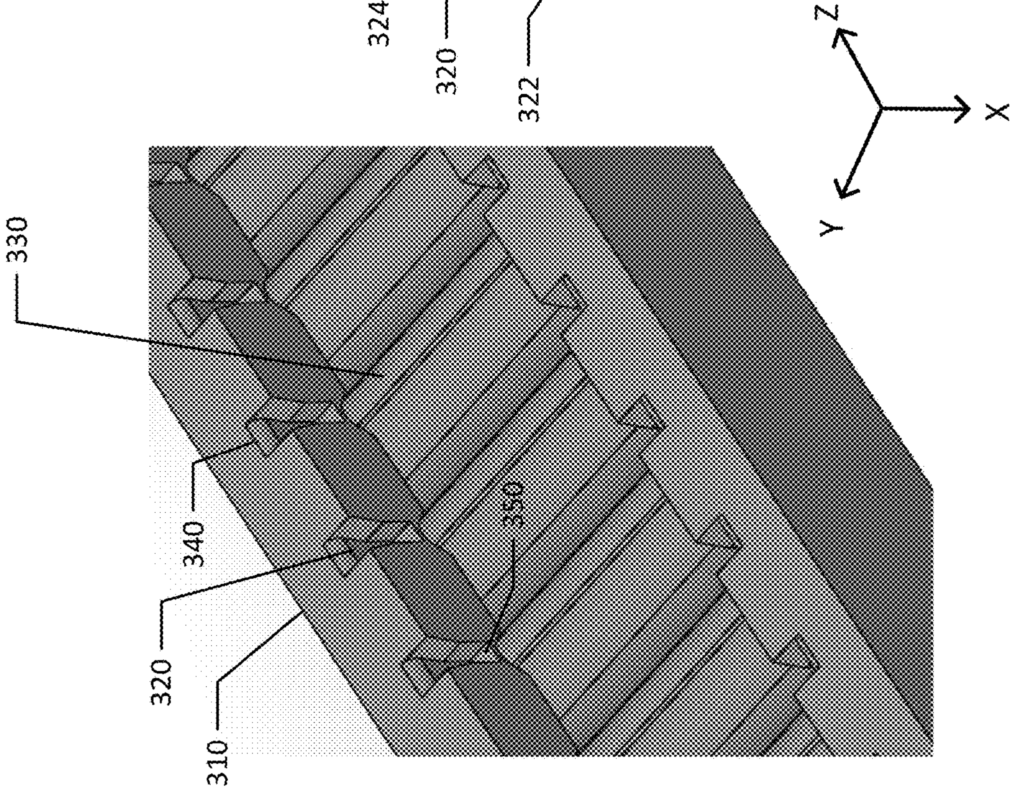
FIG. 3A is a partial perspective view of an opposing plate according to example embodiments of the present disclosure.

FIGS. 3A and 3B illustrate an example with two different shapes of guide slots 320. The guide slots 320 may have an open end 340 and a terminating end 350 closest to the opposing plate (e.g., flat back plate) 130 or a respective force concentrator 330. The guide slot 320 may be triangular shaped with a larger open end 340 that narrows as it approaches the terminating end 350. The guide slots may have angled side walls 322, 324 that approach each other towards the bottom of the slot opposite the open end 340.

Figure 3C:
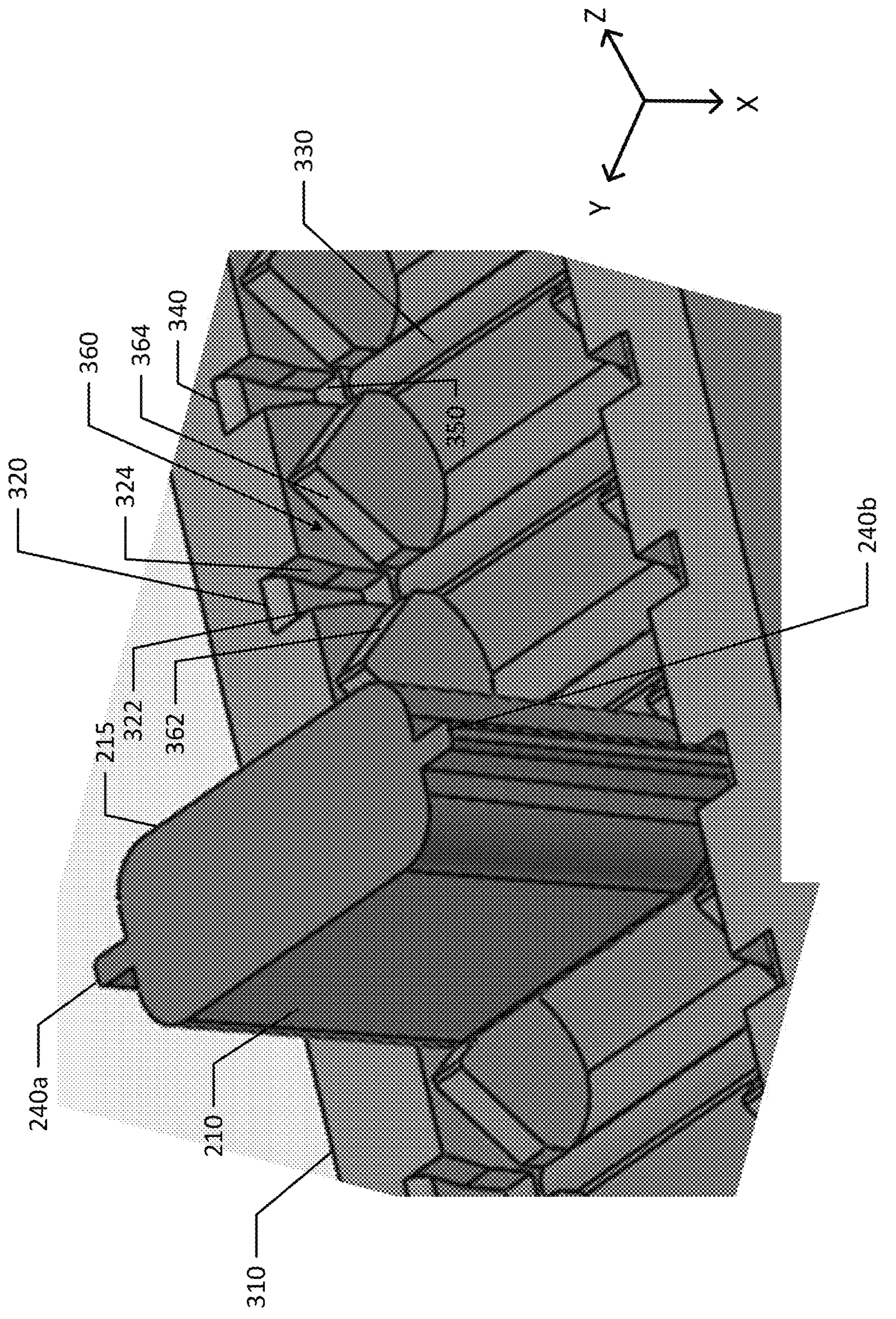
FIG. 3C is a partial perspective view of an opposing plate and pump finger according to example embodiments of the present disclosure.
Figure 3D:
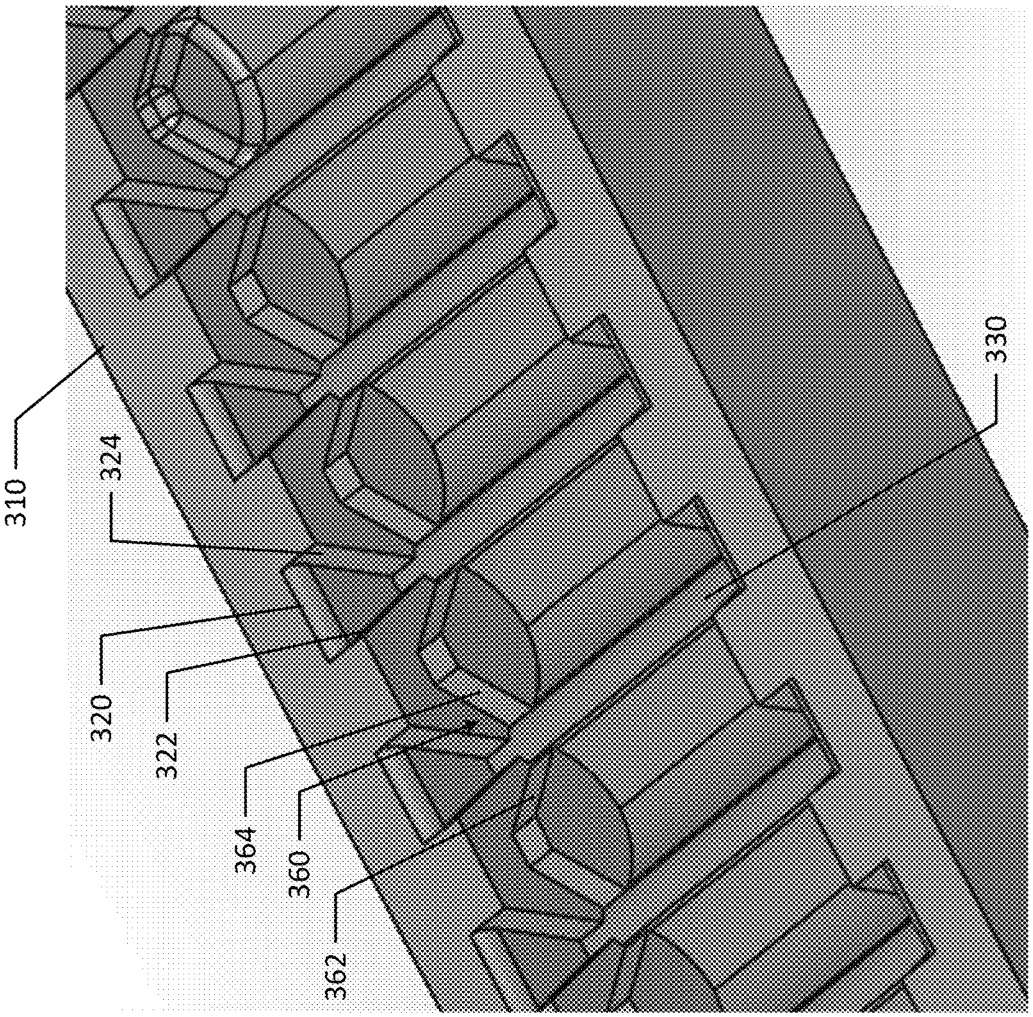
FIG. 3D is a partial perspective view of an opposing plate according to example embodiments of the present disclosure.
Figure 3E:
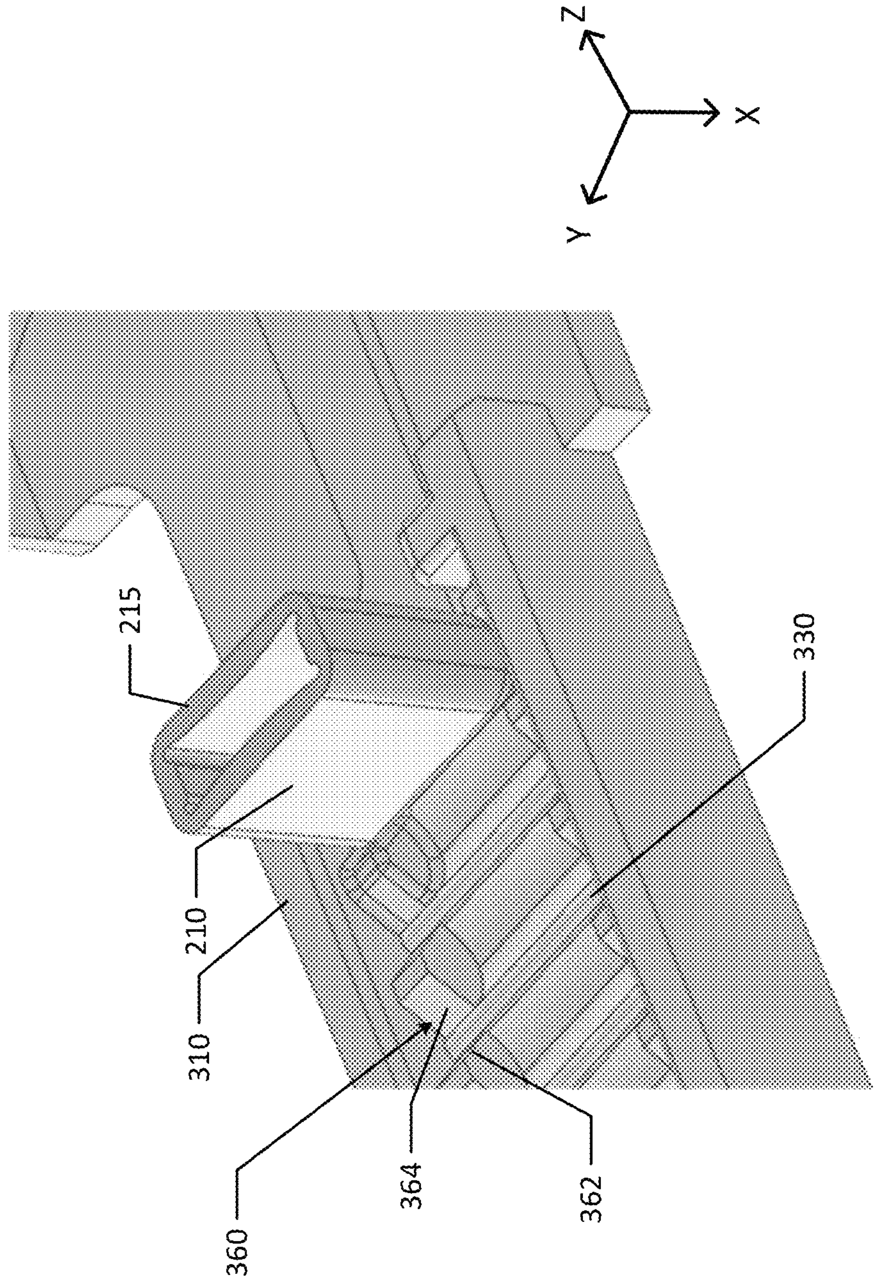
FIG. 3E is a partial perspective view of an opposing plate and pump finger according to example embodiments of the present disclosure.
Figure 3F:
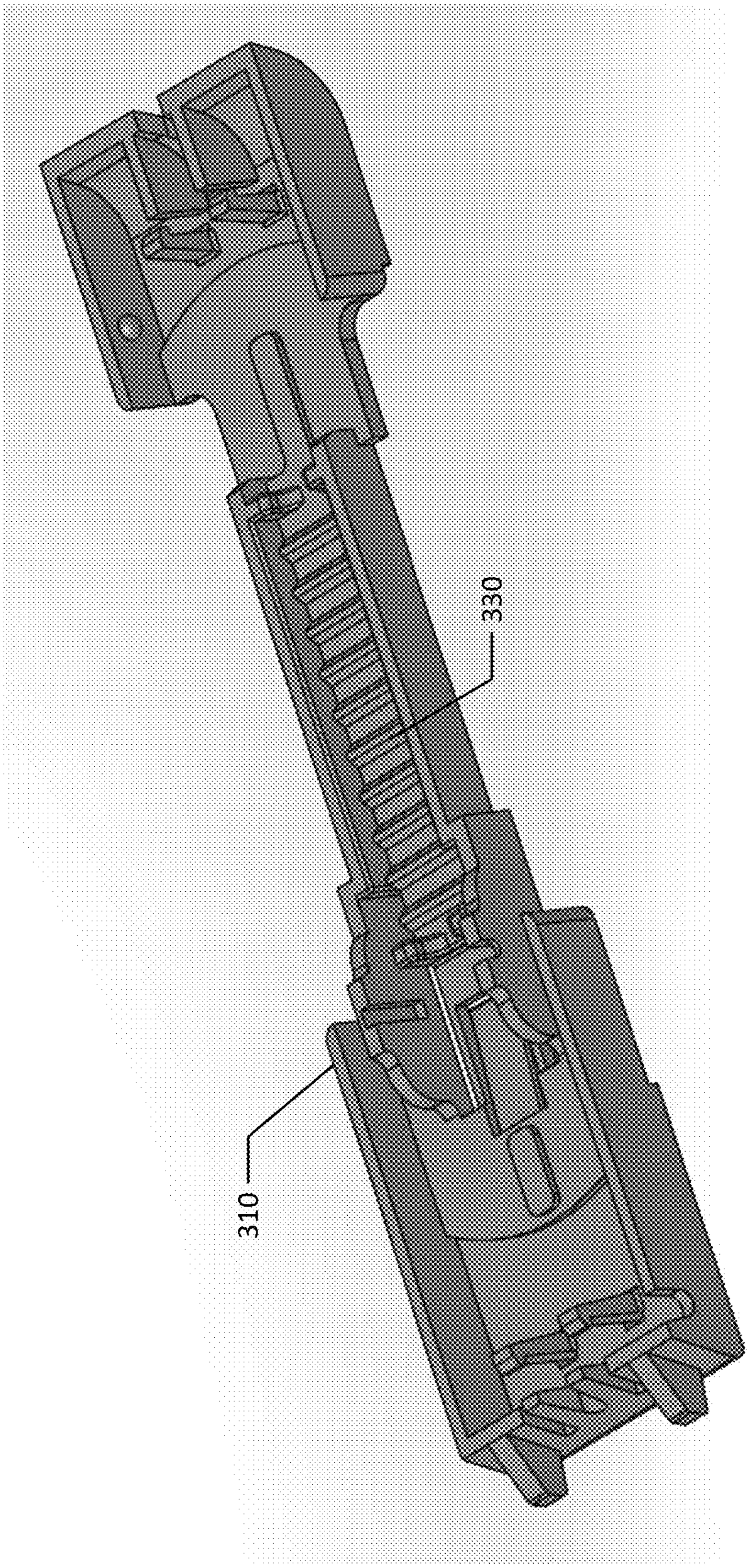
FIG. 3F is a perspective view of an opposing plate according to example embodiments of the present disclosure.

The cassette may also include guide channels 360. For example, FIGS. 3C, 3D and 3E illustrate cassettes 310 with guide channels 360. The guide channel 360 may align and guide the head portion 220 of finger 120 as the finger 120 moves to occlude tube 140 (or other pumping conduit). In some examples, the cassette may use one of the guide slots 320 or the guide channels 360. Similar to the guide slots 320, guide channels 360 may be a triangular shaped that narrows as the channel approaches the opposing plate 130 or respective force concentrator 330. The guide channels 360 may have angled side walls 362, 364 that approach each other towards the bottom of the channel. In other examples, both guide slots 320 and guide channels 360 may be included on the cassette 310 (as illustrated in FIGS. 3C and 3D) to provide multiple modes of alignment for fingers 120.

Figure 10C:
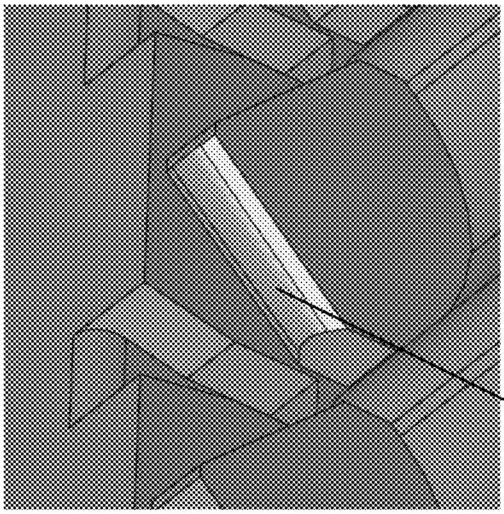
FIGS. 10A, 10B and 10C illustrate various surface profiles (e.g., flat, pointed and round) for rails, slots and channels according to an example embodiment of the present disclosure.
Figure 10B:
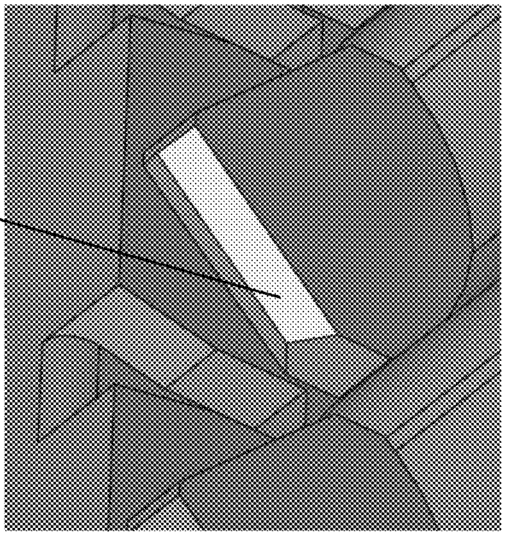
Figure 10A:
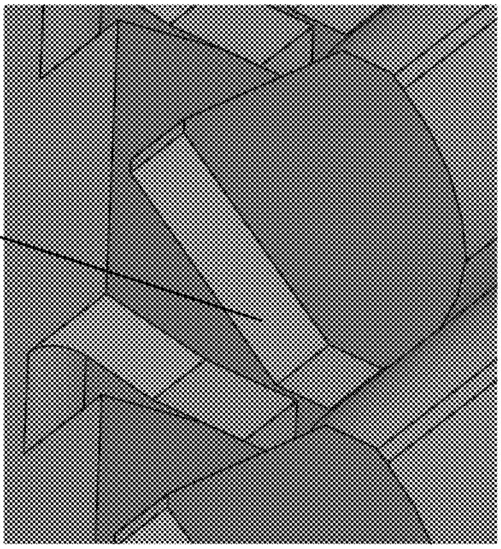

In the example illustrated in FIG. 3C, guide channels 360 may be triangular shaped corresponding to the shape of head portion 220 of fingers 120, such that as the fingers 120 advance toward the force concentrators 330. The approach angle of both the guide slots 320 and guide channels 360 may be optimized to allow for negligible friction between fingers 120 (and corresponding guide rails 240), guide slots 320 and/or guide channels 360. To provide negligible friction, the outer edges of the fingers 120, guide rails 240, guide slots 320 and/or guide channels 360 may be rounded. Furthermore, surfaces 322, 324, 362 and 364 may be rounded or pointed to provide guidance with minimum friction. Examples of flat surfaces, pointed surfaces and rounded surfaces are illustrated in FIGS. 10A, 10B and 10C respectively.

In the illustrated examples, the alignment tips or guide stops 250 enter the open ends of guide slots 320. For example, the alignment tips or guide stops 250 may serve as both an initial alignment tip and later as a guide stop 250 to limit the motion of the finger 120 in the X-direction. As the pump fingers continue to move towards the opposing plate (e.g., cassette plate or door plate), the larger guide rails 240 also enter the guide slots 320 which provides proper alignment of the pump finger 120 in the Y-Z plane. In some examples, the head portion 220 of the finger 120 is also guided and aligned in the Y-Z plane by a respective guide channel 360. Both the guide channel 360 and the guide rail 320 may align the finger 120 to ensure that the tip 230 of the finger is aligned with the corresponding concentration surfaces (e.g., tip portions) of the force concentrator 330. Occluding the tube 140 (or other pumping conduit) in the vertical X-plane extending between the tip 230 and the corresponding concentration surfaces (e.g., tip portions) of the force concentrator 330 provides two narrow surfaces for tube occlusion. Each narrow surface (e.g., tip 230 and the corresponding concentration surfaces (e.g., tip portions) of the force concentrator 330) provides more occlusion pressure to the tube 140 (or other pumping conduit) for the same amount of pressing force. For example, because the pressure against the tube wall required for occlusion is force divided by the area providing the force, the narrower surfaces provide higher pressures for the same amount of applied force.

In FIG. 3E, the finger 120 is provided without guide rail(s), but the guide channels 360 align and guide the entire finger 120 such that the tips 230 of fingers 120 are directed towards and align with force concentrators 330.

As discussed above, the pumping mechanism 100 may include various alignment features such as guide rails 240, alignment tips or guide stops 250 and/or guide slots 320 to compensate for tolerances perpendicular to finger motion. For example, the guide rails 240 may be provided for each mechanism finger 120 to minimize system tolerances in the plane perpendicular to the finger direction (of motion) (e.g., the Y-Z plane illustrated in FIGS. 2A and 2B). Providing the guide rails 240 allows for concentrators at the tip 230 of each finger 120 to be narrower because tolerance differences are minimized. The narrower the tip 230 (e.g., tips with smaller surface areas) provide higher pressure to the tube walls when pressed against the tube 140. Without guide rails 240, a finger 120 may require a relatively flat concentrator with a broader tip 230 to compensate for tolerance ranges within the system. For example, without guiding elements such as guide rails 240, the tip 230 may be as wide as 1.5 mm to compensate for tolerance ranges within the system. Conversely, guiding elements may allow for a tip that has a width of 0.75 mm or less.

The force concentrators 330 may be non-elastic or elastic. Elastomeric force concentrators advantageously compensate for tolerances along the axis of finger motion (e.g., the X-direction in FIGS. 2A and 2B). For example, to minimize tolerance effects in the X-direction (e.g., direction of finger action or motion), elastomeric force concentrators 330 may be used such that as the elastomeric concentrator 330 is compressed, the concentrator 330 acts as a spring and absorbs the tolerance stack. The elastomeric force concentrator 330 may also lower energy requirements in consequent pumping cycles as the elastomer will typically "set" after a few pump cycles and therefore will require less compression to compensate for the tolerance stack.

Figure 4:
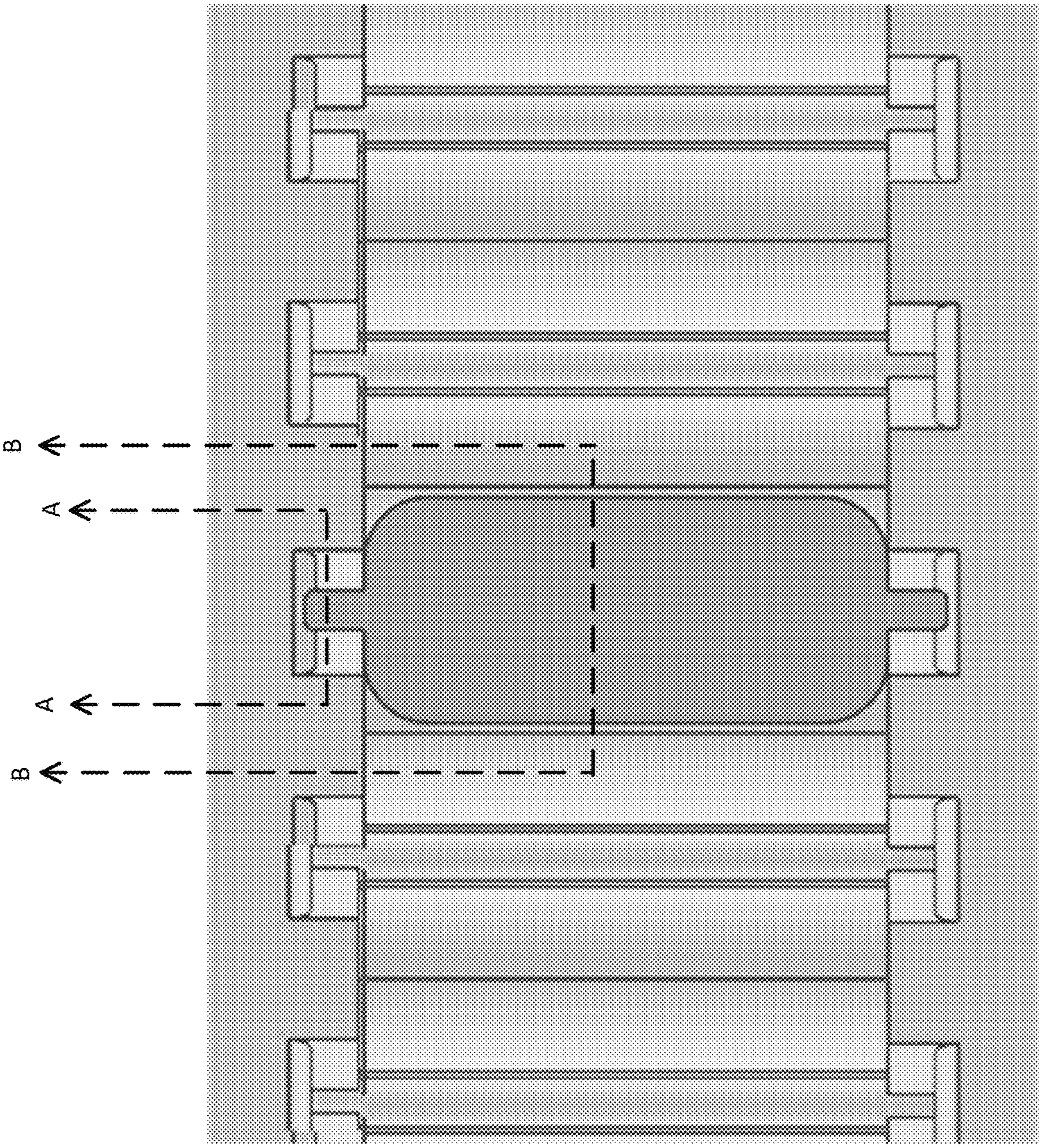
FIG. 4 is a partial top view of an opposing plate and pump finger according to example embodiments of the present disclosure.
Figure 5A:
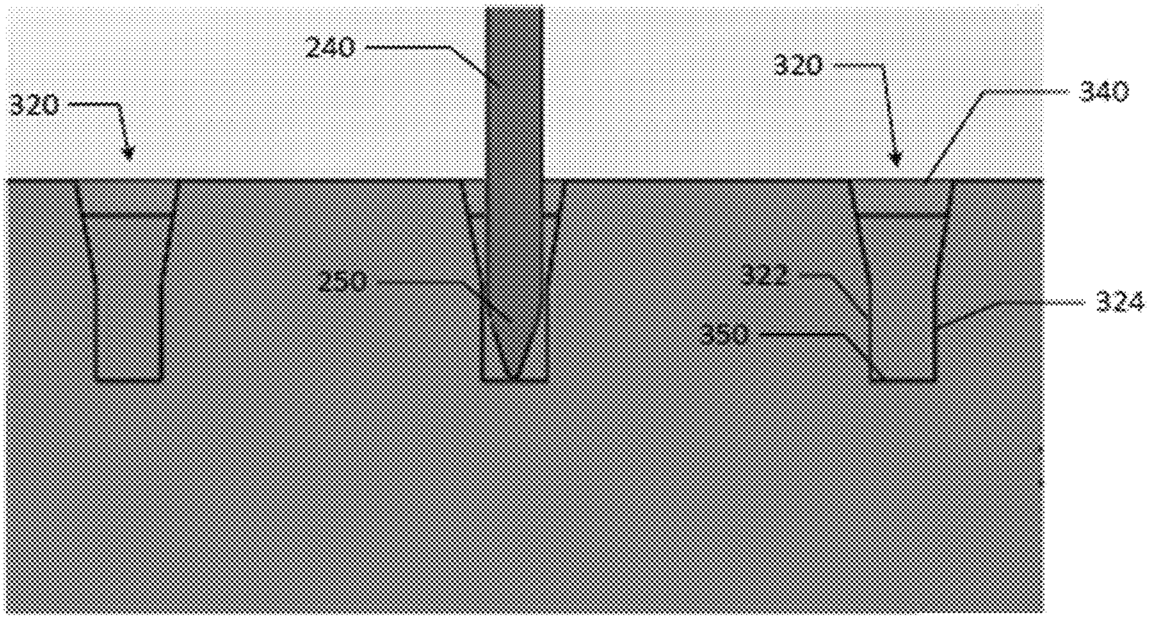
FIG. 5A is a cross-sectional view of an example opposing plate and pump finger according to an example embodiment of the present disclosure.
Figure 5B:
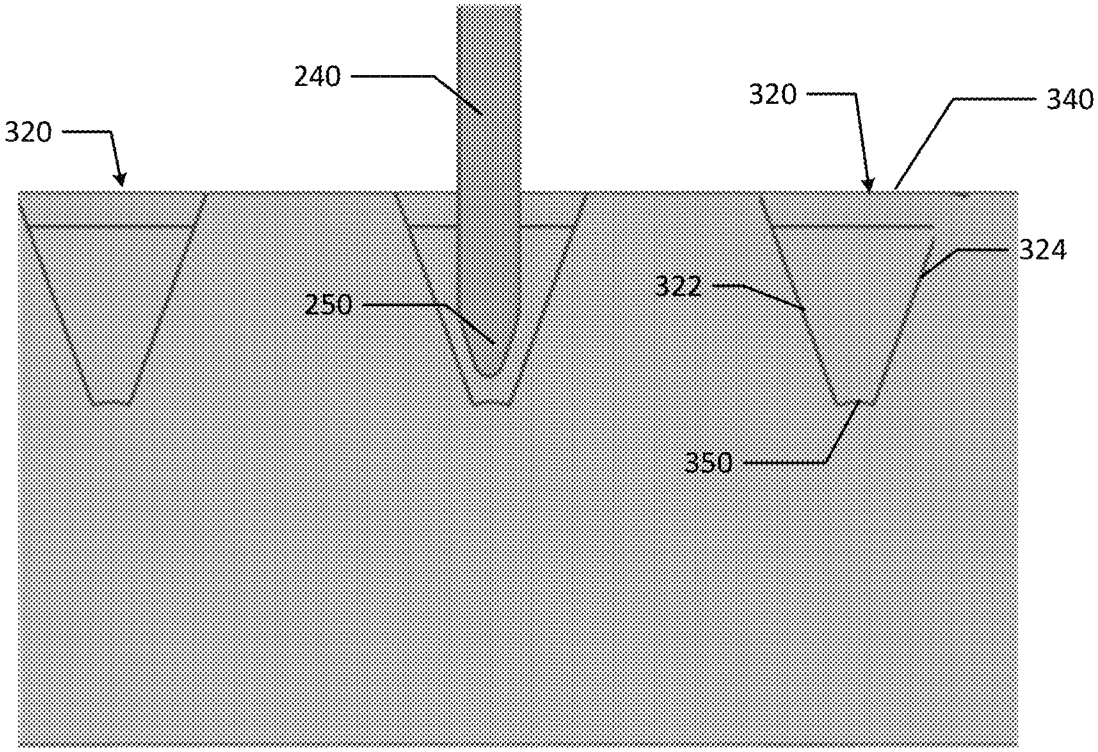
FIG. 5B is a cross-sectional view of another example opposing plate and pump finger according to an example embodiment of the present disclosure.
Figure 6A:
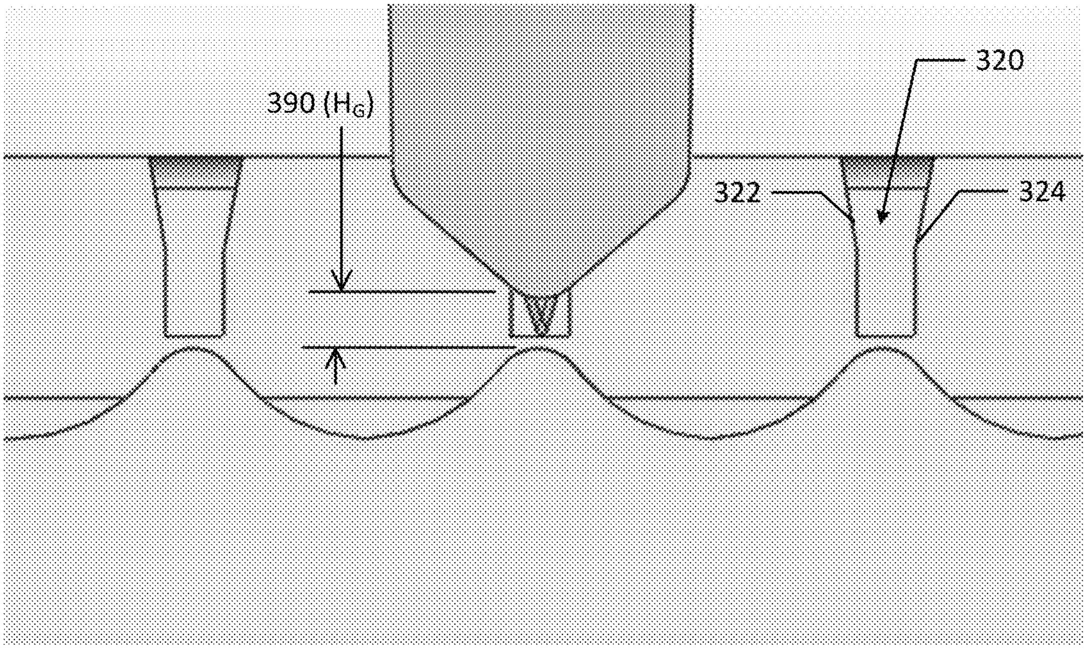
FIGS. 6A, 6B, 6C and 6D are cross-sectional views of example opposing plates and pump fingers according to example embodiments of the present disclosure.
Figure 6B:
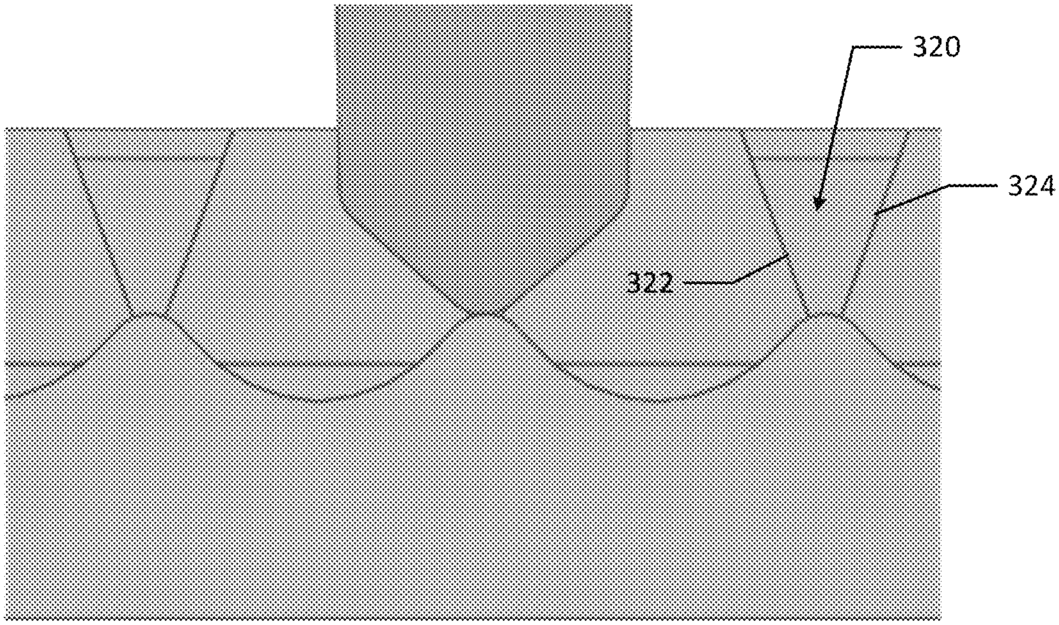

FIG. 4 illustrates a partial top view of an opposing plate and pump finger. FIGS. 5A and 5B illustrate two different examples for the cross-sectional view A-A of FIG. 4 and show different guide slot 320 geometries as well as different alignment tip or guide stop 250 geometries. FIGS. 6A and 6B illustrate two different examples for the cross-sectional view B-B of FIG. 4 and show different guide slot 320 geometries as well as different alignment tip or guide stop 250 geometries similar to those of FIGS. 5A and 5B. For example, FIGS. 5A and 6A correspond to a configuration similar to the configuration illustrated in FIG. 3A. Similarly, FIGS. 5B and 6B correspond to a configuration similar to the configuration illustrated in FIG. 3B.

Figure 6C:
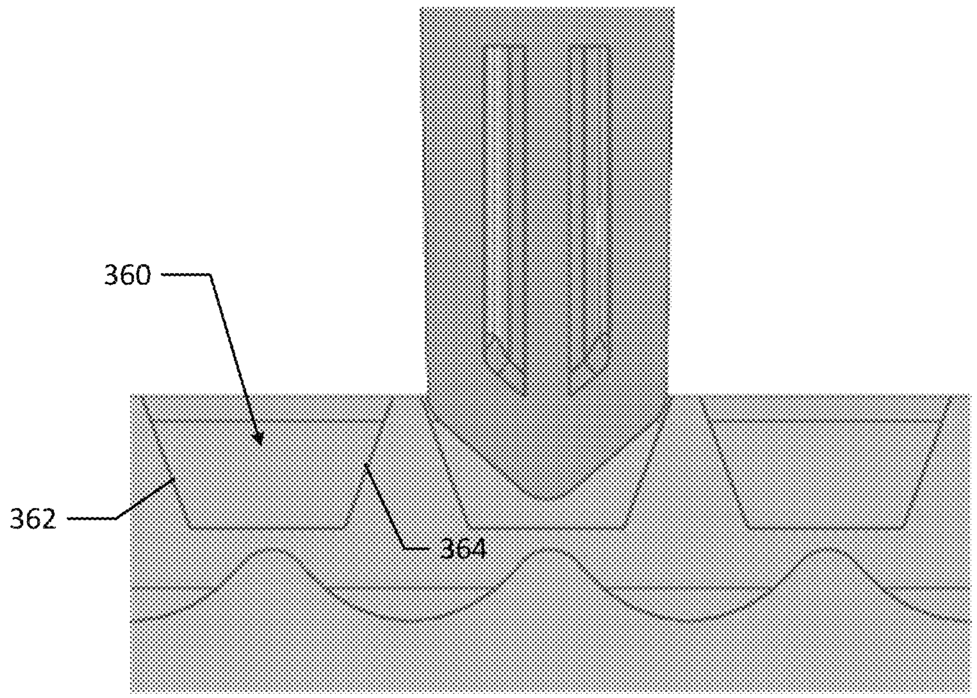
Figure 6D:
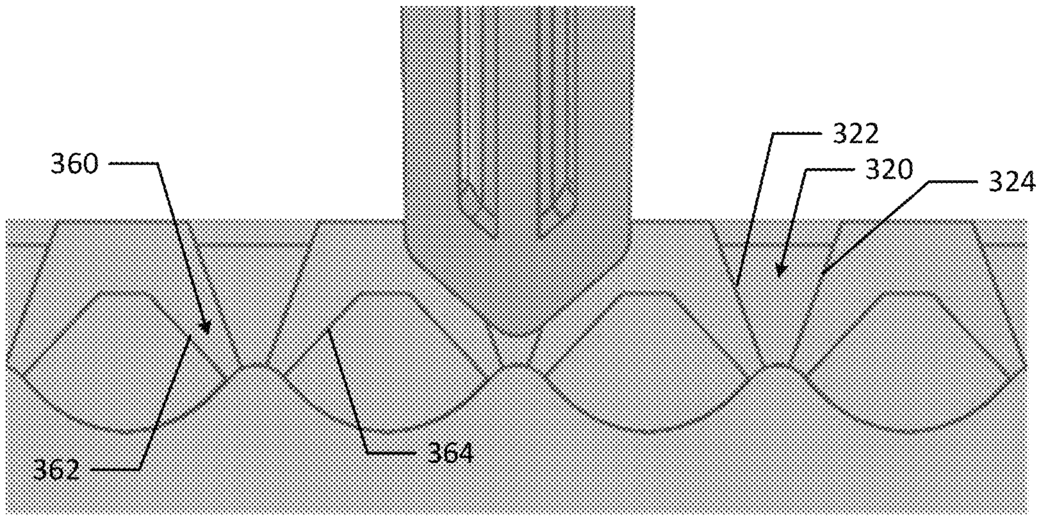

FIG. 6C illustrates an example for the cross-sectional view B-B of FIG. 4 and shows a configuration with only a guide channel 360 (similar to the configuration in FIG. 3E). FIG. 6D illustrates an example for the cross-sectional view B-B of FIG. 4 and shows a configuration with both guide slots 320 and guide channels 360 (similar to the configuration in FIG. 3C).

As illustrated in FIGS. 5A and 6A, the alignment tip 250 may be adapted to pre-align each finger 120 prior to substantial compression of the IV tube. Additionally, the alignment tip 250 may provide an extended alignment path for the guide rails 240 in areas of limited space.

In another example, the alignment tip or guide stop 250 may bottom out at the terminating end 350 of the guide slot 320 to limit the motion of the finger 120 in the X-direction. Providing a backstop or a limit to the motion of finger 120 in the X-direction provides a pre-determined gap height between the tip 230 of finger 120 and the concentration surface (e.g., tip portion) on force concentrator 330. The predetermined gap height ($H_G$) 390 may be based on one or more of the material, dimensions, wall thickness, material properties, system forces, etc. of the tube 140 (or other pumping conduit). For example, tubes 140 with thicker tube walls may have larger gap heights ($H_G$) 390. Similarly, pumping conduits with thicker membranes may have larger gap heights ($H_G$) 390.

Figure 7A:
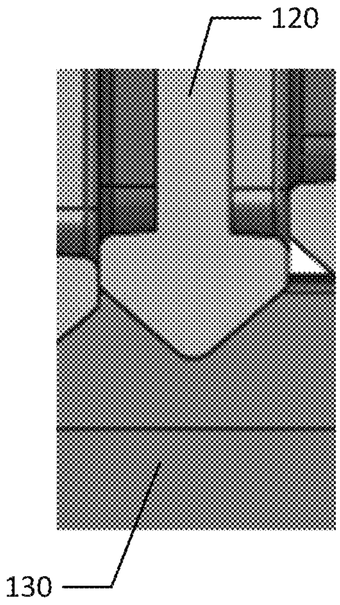
FIG. 7A is a partial side view of a pumping mechanism with a flat opposing plate according to an example embodiment of the present disclosure.
Figure 7B:
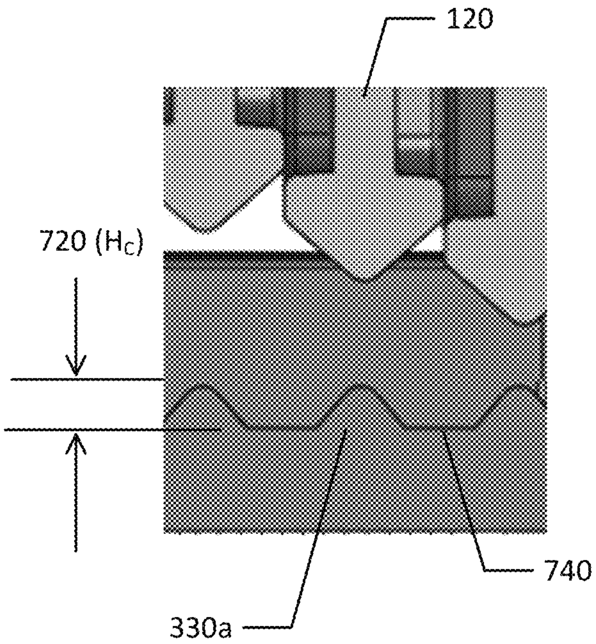
FIGS. 7B, 7C, and 7D are partial side views of pumping mechanisms with different example force concentrators according to example embodiments of the present disclosure.

FIGS. 7A, 7B, 7C and 7D illustrate four different arrangements of fingers 120 and opposing plates 130. In the example illustrated in FIG. 7A, the pumping mechanism 100 occludes a tube 140 as the finger 120 presses the tube 140 against an opposing plate (e.g., flat back plate) 130. The opposing plate may be a cassette plate or part of a door. In FIG. 7B, the pumping mechanism also utilizes force concentrators (e.g., force concentrator 330*a*) that assist with occluding the tube 140 when the finger 120 moves toward the opposing plate 130. Force concentrators 330*a* have a similar shape of opposing fingers 120 and may also include a flat base portion 740.

Figure 7C:
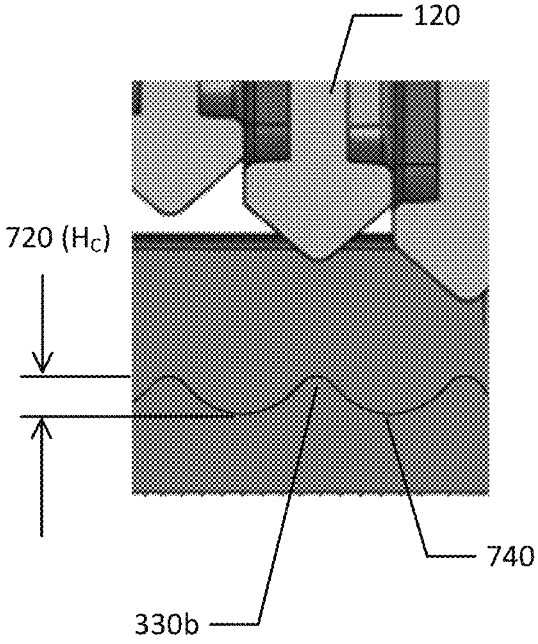

In FIG. 7C, the pumping mechanism utilizes force concentrators (e.g., force concentrators 330*b*) that assist with occluding the tube 140 (or other pumping conduit). In this configuration, the force concentrators 330*b* flow into a rounded or curved base portion 440 that may provide improved cleanability to the pump. Similarly, in FIG. 7D, the pumping mechanism utilizes force concentrators (e.g., force concentrator 330*c*) that assist with occluding the tube 140 when the finger 120 moves toward the back plate 130. The profile of the force concentrators 330*c* and rounded or curved base portion provide improved cleanability while also improving system tolerance accommodations.

Each force concentrator 330 may have a concentrator height ($H_C$) 720 and a width of the concentration surface (e.g., tip portion) ($W_S$) 710. The width ($W_S$) 710 is smaller in the configurations illustrated in FIGS. 7B and 7C, which may provide more pressure on the tube 140 (or other pumping conduit), but may also require additional alignment features or lower force under equivalent pressure.

In an example, the force concentrators 330 may be a separate component that is connected to or sits atop the opposing plate 130. In another example, the force concentrators 330 may be integrated into the opposing plate 130 as a single component. As discussed above, the force concentrators 330 may be elastomeric or non-elastomeric.

Figure 7D:
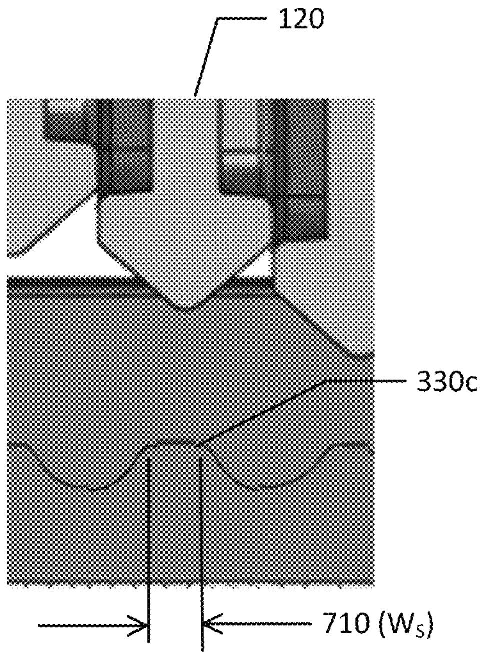

As illustrated in FIGS. 7B, 7C and 7D, the force concentrators 330 may have different surface profiles and geometries. In the example illustrated in FIG. 7B, the force concentrator 330*a* mimics the shape of the head portion 220 such that the tip 230 of head portion 220 meets a tip or concentration surface (e.g., tip portion) of the force concentrators 330*a*. The force concentrator 330*c* illustrated in FIG. 7D includes a flatter concentration surface (e.g., tip portion), which may help account for tolerance differences. For example, by providing a flatter and broader concentration surface (e.g., tip portion) on force concentrator 330*c*, the likelihood of the tip 230 of head portion 220 aligning with the concentration surface (e.g., tip portion) of force concentrator 330*c* increases.

Additionally, the pumping mechanism may include other surface profiles for the force concentrators 220 and base portions. In some examples, alternating patterns or combinations of the surface profiles illustrated in FIGS. 7A-7D may be used. Other shapes and configurations of fingers 120 and/or force concentrators 330 are possible, such as rails or guides on the opposing plate 130 and a guide channel or slot on the finger 120. Additionally, as illustrated in FIGS. 7A-7D force concentrators 330 may be of different shape and surface profiles compared to fingers 120. Different sizes, shapes and surface profiles may provide various cassette tolerance improvements.

Without a force concentrator (as illustrated in FIG. 7A), the finger force ($F_F$) is equal to the force onto the opposing plate or anvil ($F_P$) (e.g., $F_F=F_P$). With a solid plastic force concentrator, the finger force ($F_F$) is equal to the force onto the opposing plate ($F_P$) minus the force reduced by the concentrator ($F_C$) (e.g., $F_F=F_P-F_C$). With an elastomeric force concentrator, the finger force ($F_F$) is equal to the force onto the opposing plate ($F_P$) minus the force reduced by the concentrator ($F_C$) as well as the force reduced by the elastomeric concentrator ($F_E$) (e.g., $F_F=F_P-F_C-F_E$).

Each of the alignment mechanisms above assist in reducing the amount of force required to partially or fully occlude the tube 140 (or other pumping conduit). Additionally, the alignment mechanisms improve the flow rate accuracy of the pumping mechanism due to improved consistency for each pump stroke. For example, by aligning pump fingers 120 during each pump motion, dimensional differences and tolerances are compensated for, which creates consistent results with each pump motion and therefore provides improved consistency of medication displacement volume per pump action.

Sample Data

Figure 8:
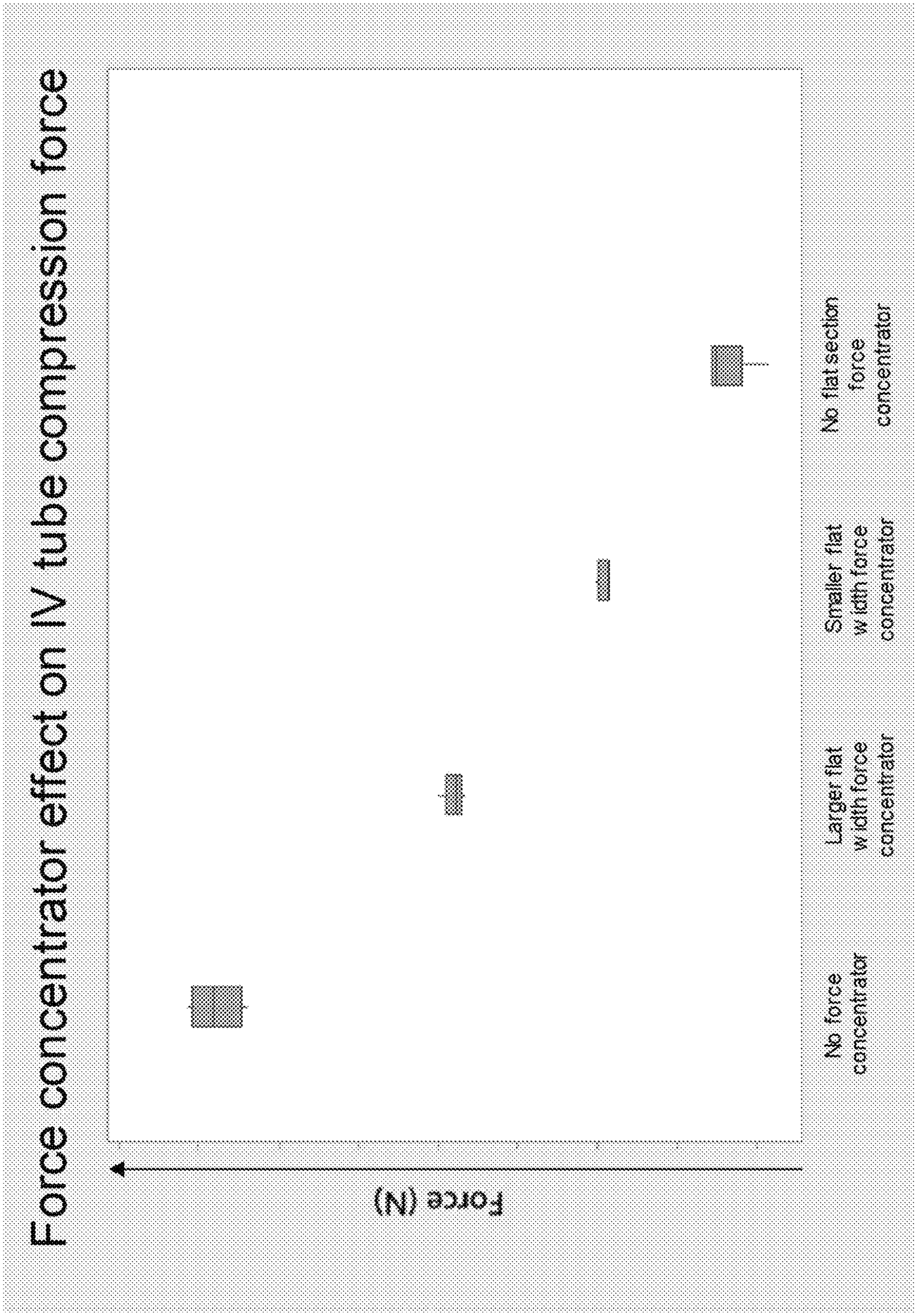
FIG. 8 illustrates a chart of pump load data according to an example embodiment of the present disclosure.

FIG. 8 is a chart illustrating the effect of tolerance compensation of finger force. A completely flat opposing plate 130 or anvil (e.g., corresponding to the design illustrated in FIG. 1A or FIG. 7A) required more force to occlude an IV tube 140, which is depicted by data set "1A" than an opposing plate 130 with force concentrators 330 (e.g., corresponding to the design illustrated in FIG. 1C). The force concentrator 330 with a tip 230 (e.g., corresponding to the design illustrated in FIG. 1C) required less force to occlude the tube 140, which is depicted by data set "1C". Typically, a force concentrator 330 with a profile corresponding to the design illustrated in FIG. 7B (e.g., with a small concentration surface width) requires the least amount of force to occlude the tube. A force concentrator 330 with a profile corresponding to the design illustrated in FIG. 7B (e.g., with a larger concentration surface width) may require more force than a force concentrator 330 that has a smaller concentration surface width (e.g., a pointed or pointy force concentrator), but less force than a completely flat opposing plate 130 or anvil to occlude the tube 140.

As illustrated in FIG. 8, without guiding elements (e.g., guide rails 240 and corresponding guide slots 320), either a flat opposing plate 130 (as illustrated in FIG. 7A) or a flatter and broader concentration surface (e.g., tip portion) on force concentrator 330*c* may be required to compensate for the tolerance stack. However, compensating for system tolerances by using a flat opposing plate 130 or a broader concentration surface (e.g., tip portion) on force concentrator 330*c* results in increased force or load needed to occlude the tube 140. Conversely, by minimizing dimensional differences and accounting for tolerances with alignment and guiding elements (e.g., guide rails 240 and corresponding guide slots 320), narrower and more pronounced tips 230 on fingers 120 as well as more pronounced and narrower concentrations surfaces on force concentrators 330 may be used to reduce the amount of force required to occlude the tube 140 loaded in the pumping mechanism 100.

Figure 9:
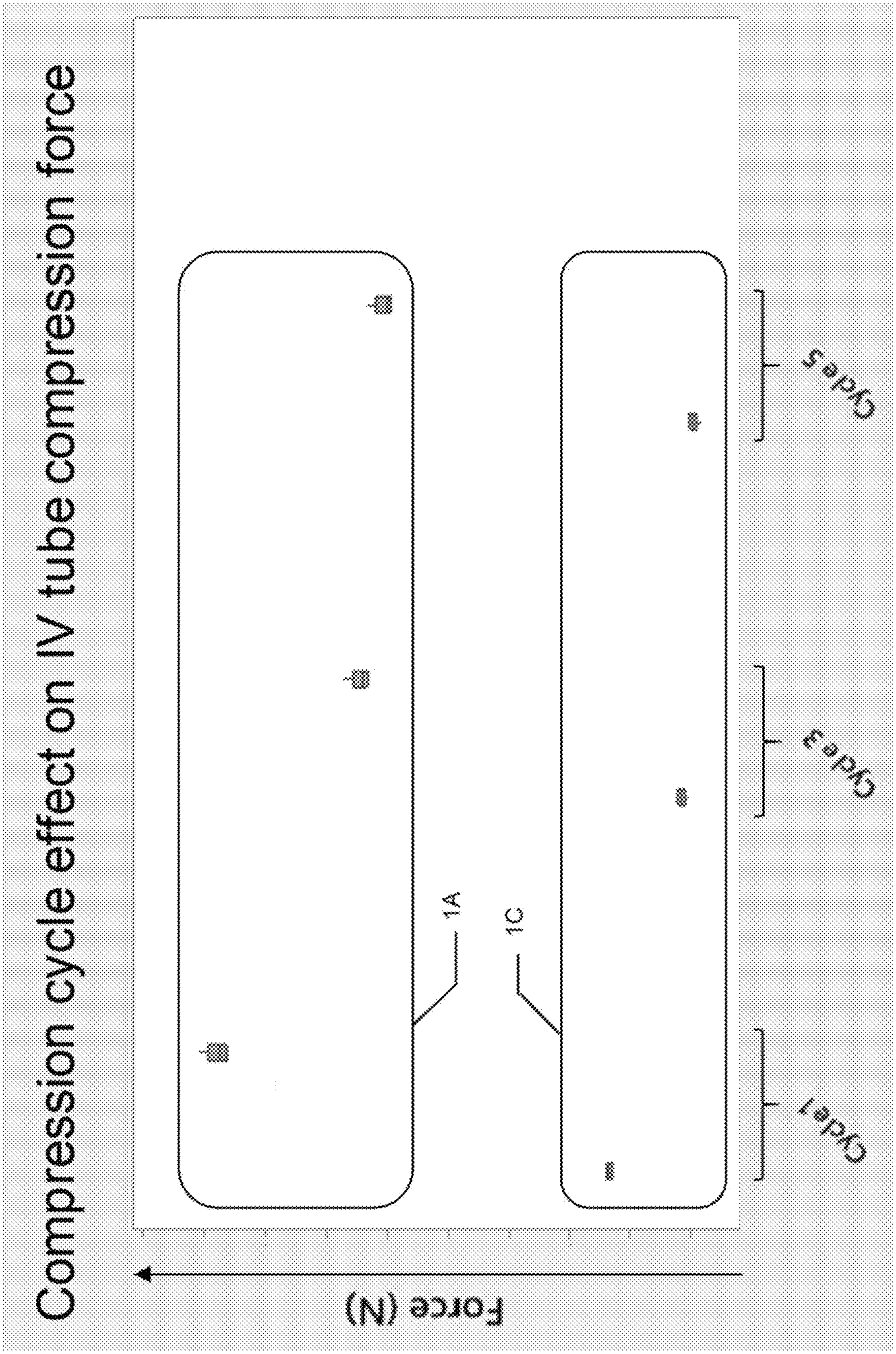
FIG. 9 illustrates a chart of pump force data according to an example embodiment of the present disclosure.

FIG. 9 illustrates a plot of forces to occlude an IV tube 140 based on different compression cycles. Occlusion forces were recorded for three different compression cycles (e.g., cycle 1, cycle 3 and cycle 5) for both a flat opposing plate 130 (see FIG. 1A) as well as an opposing plate 130 with force concentrators (see FIG. 1C). Data set "1A" corresponds to the pumping mechanism configuration illustrated in FIG. 1A and data set "1C" corresponds to the pumping mechanism configuration illustrated in FIG. 1C. Force concentrators 330 reduce IV tube compression force as shown on the plot illustrated in FIG. 9. In some cases, the IV tube compression force may be reduced by 50 percent or more when using force concentrators 330 compared to a flat opposing plate 130 (see FIG. 1A). As discussed above and referring back to FIG. 1C, the force concentrators 330 are located in the cassette in locations opposite to mechanism fingers 120.

As illustrated in FIGS. 8 and 9, force concentrators 330 reduce IV tube compression forces (e.g., by approximately 50 percent). The reduction in compression forces directly translates to other pump benefits such as (i) reduced wear on pump components due to lower system forces and torques, (ii) improved reliability of pump components due to lower system forces and torques, and (iii) extended battery life due to reduced motor power needs.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. An infusion pumping mechanism comprising:

a motor;

a plurality of pump fingers, wherein each finger includes a body portion and a head portion, and the head portion includes a pump finger tip that is configured to contact and occlude a tube installed in the pumping mechanism; and an opposing plate including an anvil with a plurality of force concentrators, wherein a force concentrator of the plurality of force concentrators corresponds to a respective pump finger of the plurality of pump fingers, the force concentrator includes a concentration surface configured to contact and occlude the tube, wherein the concentration surface comprises a force concentrator tip, and the force concentrator tip is aligned with one of the pump finger tips of the plurality of pump fingers such that as the finger is directed towards the tube and contacts the tube, both the pump finger tip and the force concentrator tip provide pressure to opposite sides of the tube and at least partially occlude the tube.

2. The pumping mechanism of claim 1, wherein the infusion pumping mechanism is part of an infusion pump.

3. The pumping mechanisms of claim 2, wherein the infusion pump is an ambulatory infusion pump.

4. The pumping mechanism of claim 1, wherein each finger includes a guide rail and the opposing plate includes corresponding guide slots.

5. The pumping mechanism of claim 1, wherein the opposing plate includes at least one of a guide slot and a guide channel and each finger includes corresponding guide rails.

6. The pumping mechanism of claim 1, wherein the opposing plate includes guide channels corresponding to each pump finger of the plurality of pump fingers.

7. The pumping mechanism of claim 6, wherein the guide channel is sized and shaped to receive a portion of a respective pump finger, and wherein the guide channel is configured to align the pump finger to direct the tip of the respective pump finger towards a corresponding force concentrator.

8. The pumping mechanism of claim 1, wherein each finger includes a guide rail, the opposing plate includes corresponding guide slots, and the opposing plate includes guide channels.

9. The pumping mechanism of claim 8, wherein the guide channel is sized and shaped to receive a portion of a respective pump finger, and wherein the guide slot is sized and shaped to receive at least a portion of a respective guide rail to direct the tip of the respective pump finger towards a corresponding force concentrator.

10. The pumping mechanism of claim 1, wherein each respective force concentrator is made of one of (i) an elastic material and (ii) a non-compressible material such that each respective force concentrator made of non-compressible material is non-compressible.

11. An infusion pump comprising:

a power source;

a pumping mechanism, wherein the pumping mechanism includes at least one pump finger and an opposing plate with at least one force concentrator; and an infusion tube set with a pumping conduit, wherein the at least one pump finger includes a body portion and a head portion, and the head portion includes a pump finger tip that is configured to contact and occlude the pumping conduit, the at least one force concentrator is axially aligned with the at least one pump finger, the at least one force concentrator includes a concentration surface configured to contact and occlude the pumping conduit opposite of the pump finger tip of the at least one pump finger, wherein the concentration surface comprises a force concentrator tip aligned with the pump finger tip.

12. The infusion pump of claim 11, wherein the infusion pump is an ambulatory infusion pump.

13. The infusion pump of claim 11, wherein the opposing plate includes at least one of a guide channel and a guide slot.

14. The infusion pump of claim 13, wherein the at least one pump finger includes a guide rail corresponding to at least one of the guide channel and the guide slot.

15. The infusion pump of claim 11, wherein the at least one pump finger includes a guide rail.

16. The infusion pump of claim 15, wherein the opposing plate includes a guide slot corresponding to the guide rail.

17. The infusion pump of claim 15, wherein the opposing plate includes at least one guide channel corresponding to the at least one pump finger.

18. The infusion pump of claim 17, wherein the at least one guide channel is sized and shaped to receive a portion of the at least one pump finger, and wherein the guide slot is sized and shaped to receive the guide rail to direct the tip of the respective pump finger towards a corresponding force concentrator.

19. The infusion pump mechanism of claim 11, wherein the pumping conduit comprises a tube.

20. The infusion pump mechanism of claim 11, wherein the pumping conduit includes a silicon membrane.

* * * * *